(12) United States Patent
Bonadio et al.

(10) Patent No.: US 8,752,553 B2
(45) Date of Patent: Jun. 17, 2014

(54) APPARATUS FOR USE IN SURGERY AND A VALVE

(75) Inventors: Frank Bonadio, Bray (IE); Alan Reid, Clontarf (IE)

(73) Assignee: Atropos Limited, County Wicklow (IE)

( * ) Notice: Subject to any disclaimer, the term of this patent is extended or adjusted under 35 U.S.C. 154(b) by 1925 days.

(21) Appl. No.: 10/600,812

(22) Filed: Jun. 20, 2003
(Under 37 CFR 1.47)

(65) Prior Publication Data
US 2004/0215063 A1    Oct. 28, 2004

Related U.S. Application Data

(63) Continuation of application No. 08/641,811, filed on May 2, 1996, now abandoned, which is a continuation of application No. PCT/IE94/00045, filed on Sep. 6, 1994.

(30) Foreign Application Priority Data

Sep. 6, 1993  (IE) .......................................... 930649
Sep. 6, 1993  (IE) .......................................... 930650

(51) Int. Cl.
*A61B 19/08* (2006.01)
*A61B 19/00* (2006.01)
*A61M 5/32* (2006.01)
*A61B 1/32* (2006.01)

(52) U.S. Cl.
USPC ........... 128/850; 128/849; 604/174; 600/203; 600/208

(58) Field of Classification Search
USPC .......... 128/849, 850; 606/108, 191, 213, 215, 606/205–207; 600/206, 208, 217; 604/174, 604/175, 16–167
See application file for complete search history.

(56) References Cited

U.S. PATENT DOCUMENTS

| | | | |
|---|---|---|---|
| 1,157,202 A | 10/1915 | McLeland |
| 1,598,284 A | 8/1926 | Kinney |
| 1,810,466 A | 6/1931 | Deutsch |
| 2,219,564 A | 10/1940 | Reyniers |
| 2,305,289 A | 12/1942 | Coburg |

(Continued)

FOREIGN PATENT DOCUMENTS

| | | |
|---|---|---|
| DE | 37 39 532 | 12/1988 |
| DE | 37 37 121 | 5/1989 |

(Continued)

OTHER PUBLICATIONS

Office Action mailed Feb. 26, 2008 in Japanese Application No. 2007-029877.

Applicants-created index of interference No. 104,195, between Leahy et al. (Senior Party) (U.S. Patent No. 5,640,977) and Bonadio et al. (Junior Party) (U.S. Appl. No. 08/641,811) and original copy from Interference File (Form PTO-257(A)).

(Continued)

*Primary Examiner* — Patricia Bianco
(74) *Attorney, Agent, or Firm* — Bookoff McAndrews, PLLC

(57) ABSTRACT

Apparatus for use in surgery comprises a sleeve (1) having an entry opening (4) at an outer end and an exit opening (5) at an inner end to access a patient's body. Exit sealing means (10) are provided for sealing the exit opening (5) to a body. Entry sealing means (20) are provided for sealing the outer entry against an arm passing therethrough to create a controlled environment within the sleeve. A valve (101) comprises an outer ring (105,106) and a sealing sleeve (107) of flexible material mounted to the ring (105,106) and extending into the opening defined by the ring to terminate in a substantially centrally disposed inlet opening (108).

29 Claims, 9 Drawing Sheets

(56) References Cited

U.S. PATENT DOCUMENTS

| | | |
|---|---|---|
| 2,695,608 A | 11/1954 | Gibbon |
| 2,835,253 A | 5/1958 | Borgeson |
| 3,111,943 A | 11/1963 | Orndorff |
| 3,244,169 A | 4/1966 | Baxter |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,522,800 A | 8/1970 | Lesser |
| 3,523,534 A | 8/1970 | Nolan |
| 3,570,475 A | 3/1971 | Weinstein |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,841,332 A | 10/1974 | Treacle |
| 3,907,389 A | 9/1975 | Cox et al. |
| 3,915,171 A | 10/1975 | Shermeta |
| 3,965,890 A | 6/1976 | Gauthier |
| 4,024,872 A | 5/1977 | Muldoon |
| 4,030,500 A | 6/1977 | Ronnquist |
| 4,096,853 A | 6/1978 | Weigand |
| 4,130,113 A | 12/1978 | Graham |
| 4,188,945 A | 2/1980 | Wenander |
| 4,228,792 A | 10/1980 | Rhys-Davies |
| 4,239,036 A | 12/1980 | Krieger |
| 4,367,728 A | 1/1983 | Mutke |
| 4,399,816 A | 8/1983 | Spangler |
| 4,434,791 A | 3/1984 | Darnell |
| 4,485,490 A | 12/1984 | Akers et al. |
| 4,550,713 A | 11/1985 | Hyman |
| 4,553,537 A | 11/1985 | Rosenberg |
| 4,601,710 A | 7/1986 | Moll |
| 4,654,030 A | 3/1987 | Moll et al. |
| 4,777,943 A | 10/1988 | Chvapil |
| 4,889,107 A | 12/1989 | Kaufman |
| 4,895,565 A | 1/1990 | Hillstead |
| 4,903,710 A | 2/1990 | Jessamine et al. |
| 4,950,222 A | 8/1990 | Scott et al. |
| 4,984,564 A | 1/1991 | Yuen |
| 4,991,593 A | 2/1991 | LeVahn |
| 4,998,538 A | 3/1991 | Charowsky et al. |
| 5,041,095 A | 8/1991 | Littrell |
| 5,045,070 A | 9/1991 | Grodecki et al. |
| D320,658 S | 10/1991 | Quigley et al. |
| 5,125,897 A | 6/1992 | Quinn et al. |
| 5,158,553 A | 10/1992 | Berry et al. |
| 5,159,921 A | 11/1992 | Hoover |
| 5,161,773 A | 11/1992 | Tower |
| 5,178,162 A | 1/1993 | Bose |
| 5,188,595 A | 2/1993 | Jacobi |
| 5,211,370 A | 5/1993 | Powers |
| 5,213,114 A | 5/1993 | Bailey, Jr. |
| 5,234,455 A | 8/1993 | Mulhollan |
| 5,248,304 A | 9/1993 | Vigdorchik et al. |
| 5,263,922 A | 11/1993 | Sova et al. |
| D343,236 S | 1/1994 | Quigley et al. |
| D346,022 S | 4/1994 | Quigley et al. |
| 5,299,582 A | 4/1994 | Potts |
| 5,309,896 A | 5/1994 | Moll et al. |
| 5,316,541 A | 5/1994 | Fischer |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,391,156 A | 2/1995 | Hildwein et al. |
| 5,429,609 A | 7/1995 | Yoon |
| 5,480,410 A | 1/1996 | Cuschieri et al. |
| 5,514,133 A | 5/1996 | Golub et al. |
| 5,522,791 A | 6/1996 | Leyva |
| 5,524,644 A | 6/1996 | Crook |
| 5,526,536 A | 6/1996 | Cartmill |
| 5,545,179 A | 8/1996 | Williamson, IV |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,672,168 A | 9/1997 | de la Torre et al. |
| 5,707,703 A | 1/1998 | Rothrum et al. |
| 5,741,234 A | 4/1998 | Aboul-Hosn |
| 5,741,298 A | 4/1998 | MacLeod |
| 5,755,660 A | 5/1998 | Tyagi |
| 5,769,783 A | 6/1998 | Fowler |
| 5,803,921 A | 9/1998 | Bonadio |
| 5,810,721 A | 9/1998 | Mueller et al. |
| 5,813,409 A | 9/1998 | Leahy et al. |
| 5,853,395 A | 12/1998 | Crook et al. |
| 5,899,208 A | 5/1999 | Bonadio |
| 5,906,577 A | 5/1999 | Beane et al. |
| 5,947,922 A | 9/1999 | MacLeod |
| 5,957,913 A | 9/1999 | de la Torre et al. |
| 5,964,781 A | 10/1999 | Mollenauer et al. |
| 5,997,515 A | 12/1999 | de la Torre et al. |
| 6,048,309 A | 4/2000 | Flom et al. |
| 6,110,154 A | 8/2000 | Shimomura et al. |
| 6,142,935 A | 11/2000 | Flom et al. |
| 6,142,936 A | 11/2000 | Beane et al. |
| 6,163,949 A | 12/2000 | Neuenschwander |
| 6,183,486 B1 | 2/2001 | Snow et al. |
| 6,254,534 B1 | 7/2001 | Butler et al. |
| 6,346,074 B1 | 2/2002 | Roth |
| 6,578,577 B2 | 6/2003 | Bonadio et al. |
| 6,582,364 B2 | 6/2003 | Butler et al. |
| 6,623,426 B2 | 9/2003 | Bonadio et al. |
| 6,846,287 B2 | 1/2005 | Bonadio et al. |

FOREIGN PATENT DOCUMENTS

| | | |
|---|---|---|
| DE | 296 00 939 | 6/1998 |
| EP | 0142262 | 5/1985 |
| EP | 0537768 | 4/1993 |
| EP | 0 458 989 B1 | 11/1997 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 1005557 | 1/1989 |
| JP | 10-108868 | 4/1998 |
| SU | 1342485 A1 | 1/1987 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |

OTHER PUBLICATIONS

Paper No. 23 from interference No. 104,195 (Decisions on Motion; New Preliminary Motion Period; etc.).

Paper No. 38 from interference No. 104,195 (Show Cause Order).

Paper No. 39 from interference No. 104,195 (Judgment Favorable Senior Party).

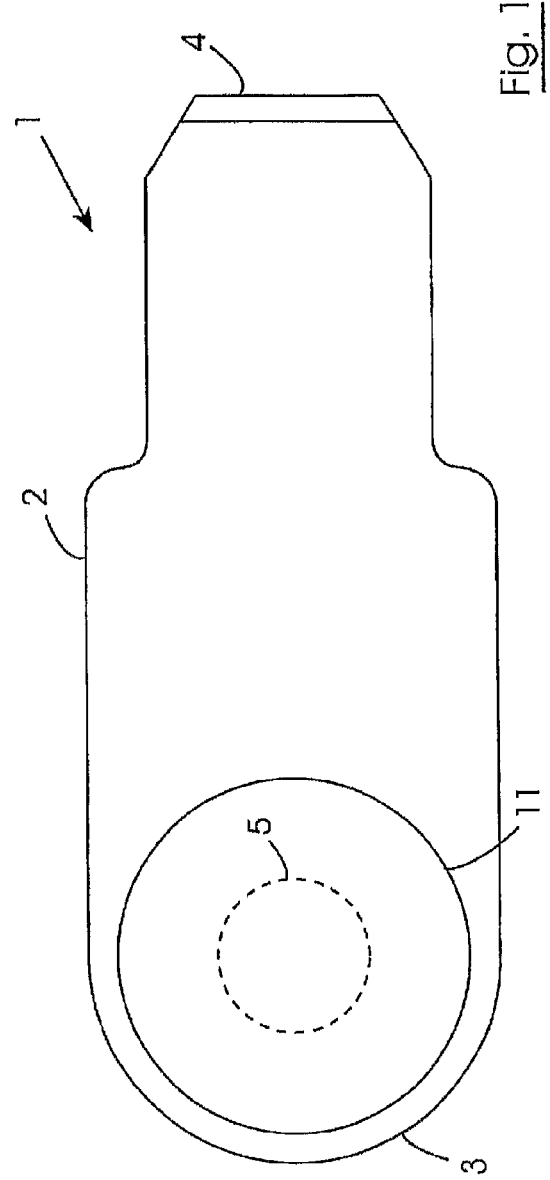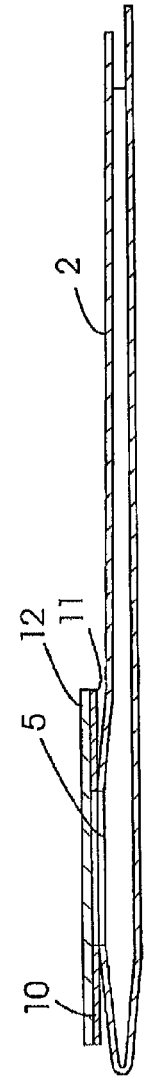

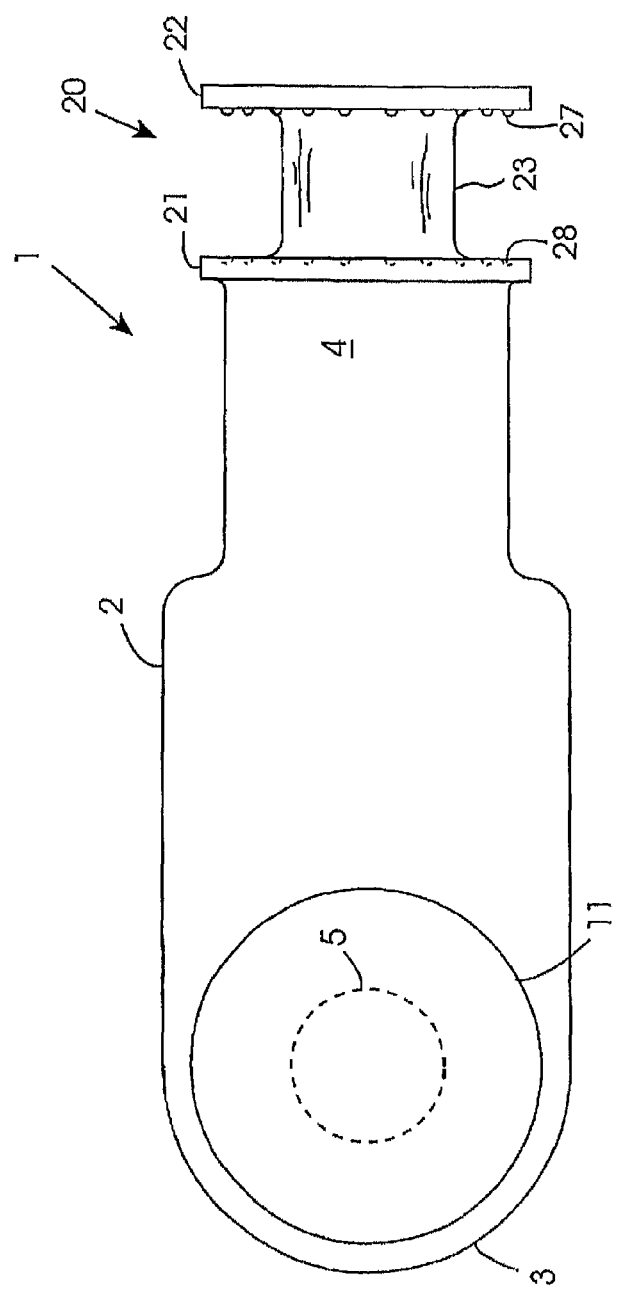

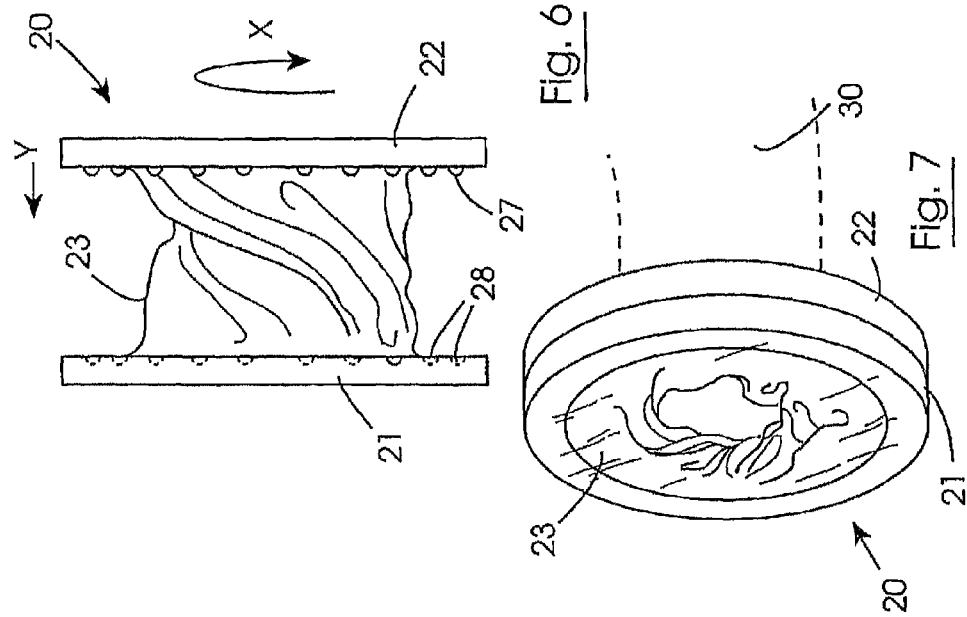
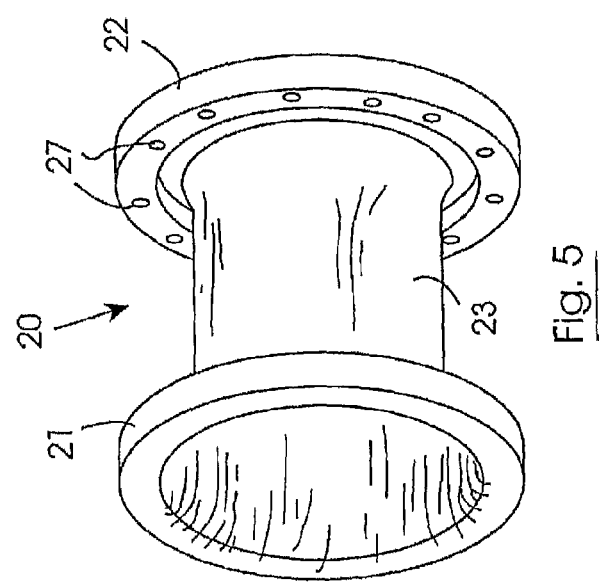

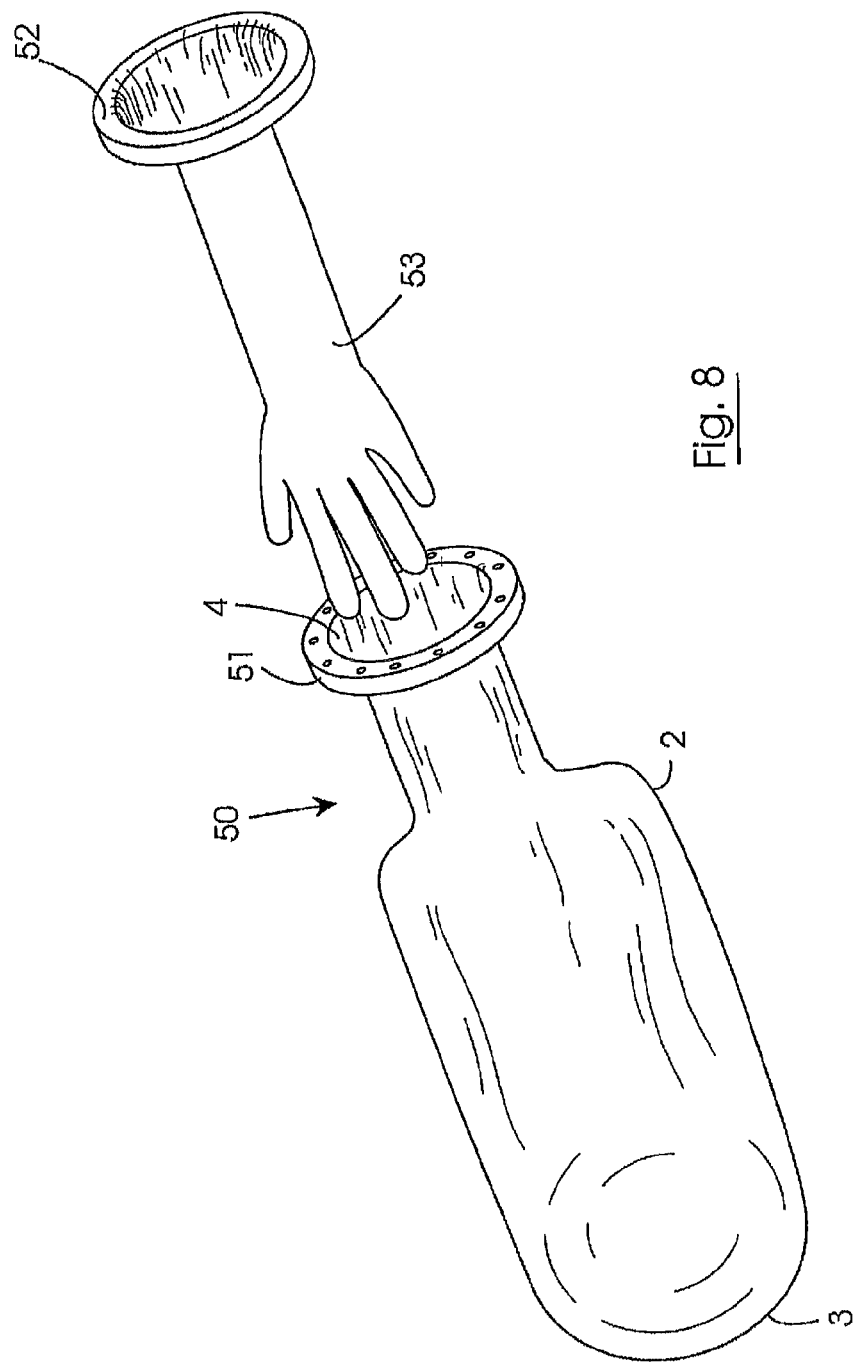

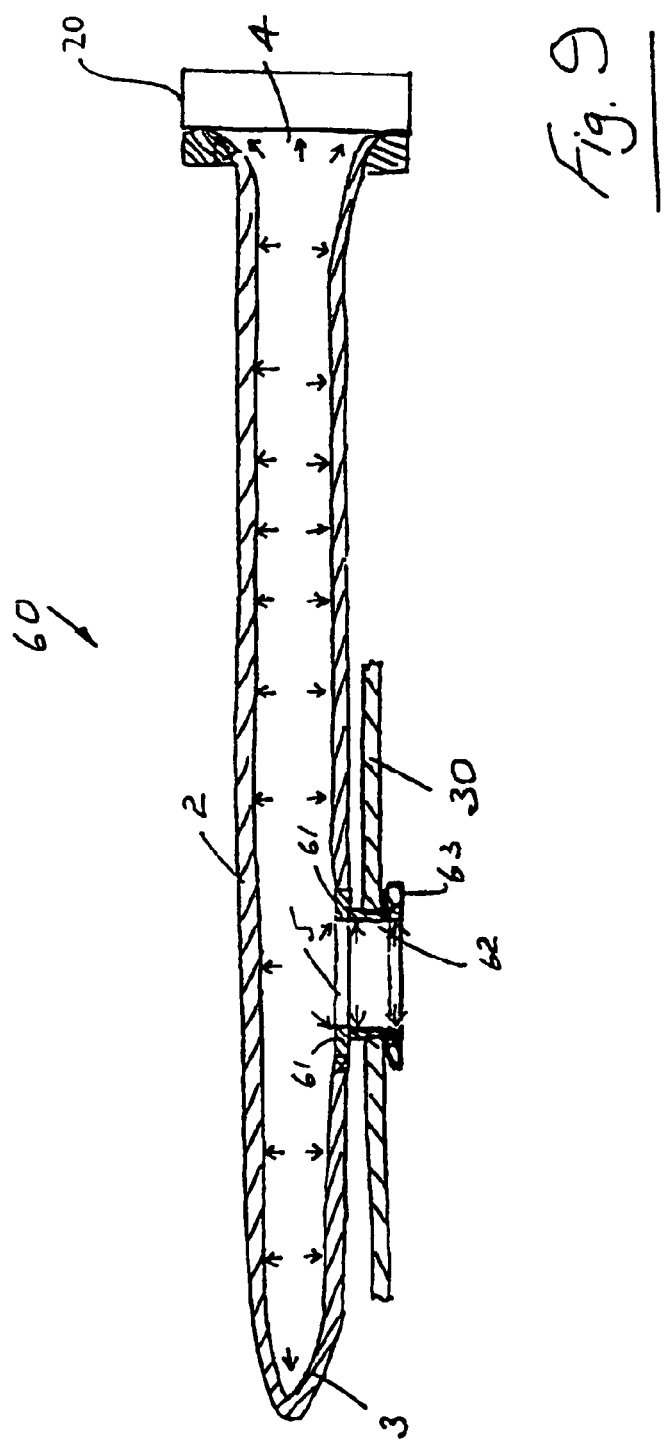

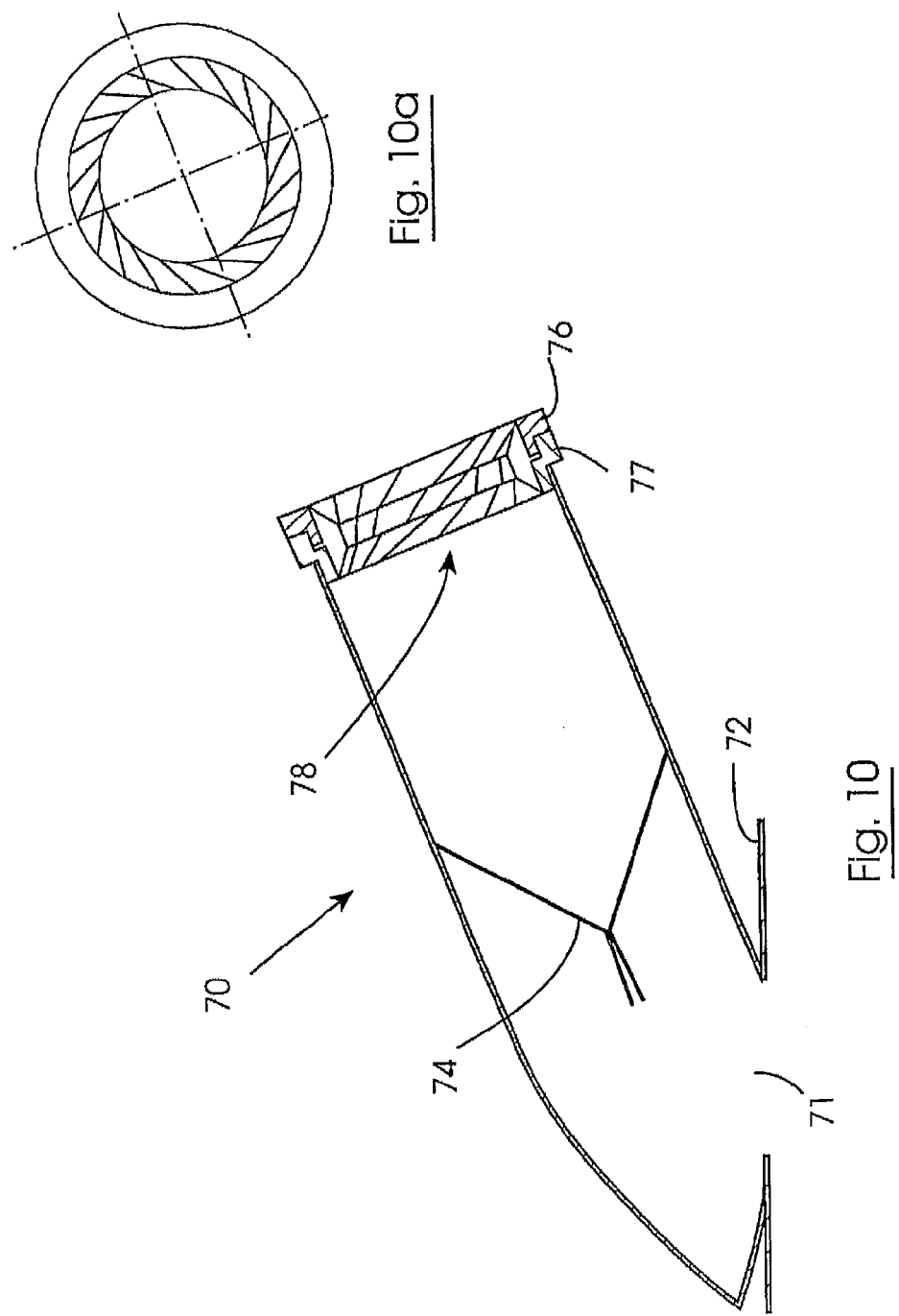

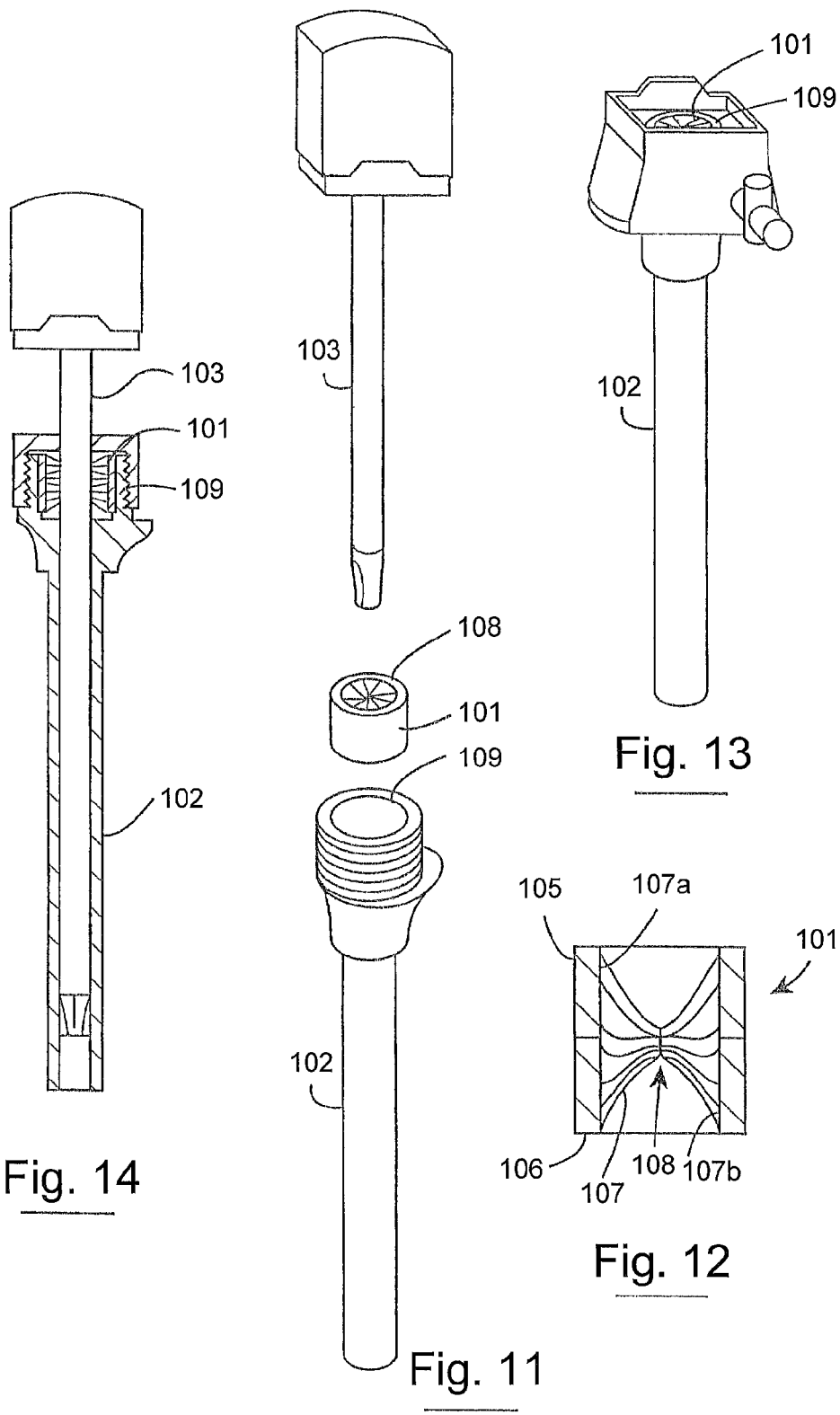

APPARATUS FOR USE IN SURGERY AND A VALVE

This application is a Continuation of U.S. patent application Ser. No. 08/641,811, filed May 2, 1996, now Abandoned, which is a Continuation of PCT/IE94/00045, filed Sep. 6, 1994. This application also claims Foreign Priority to Irish Patent Application No. 930649, filed Sep. 6, 1993 and Irish Patent Application No. 930650, filed Sep. 6, 1993.

The invention relates to an apparatus for use in surgery and in particular to an apparatus to be used in minimal invasive surgery in which surgery is carried out by making the minimum number of incisions in a patient's body.

The invention also relates to valve, and in particular to a valve for use with a trocar assembly.

Abdominal surgery is generally carried out by making a very large incision allowing a surgeon to enter the body cavity with both hands. Such surgery is traumatic for the patient and the healing process is lengthy. Some laproscopic surgery such as hernia operations may be carried out by surgeons using minimal invasive techniques with trocar assemblies. However, the techniques are generally complex and difficult and are not widely used.

Trocars are short pointed instruments used to puncture a body cavity. A cannula may be inserted into the opening created by a trocar to drain the fluids from the body. Trocars may also be used during endoscopic procedures. Trocar assemblies are described in U.S. Pat. Nos. 4,601,710 and 4,654,030.

Because of the wide range of instruments which pass through trocar tubes or trocar assemblies, a large variety of different diameter tubes and instruments are required. Various attempts have been made to provide a valve to allow a range of different sizes of instruments to pass through a single trocar tube. These efforts to date however have not been entirely successful.

There is therefore a need for an improved valve particularly for a trocar tube or cannula which will overcome this problem. This invention is directly towards providing such a valve.

According to one aspect of the invention there is provided an apparatus for use in surgery comprising a sleeve having an entry opening at an outer end thereof and an exit opening at an inner end thereof to access a patient's body, exit sealing means being provided for sealing the exit opening to a body and entry sealing means being provided for sealing the outer entry against an arm passing therethrough to create a controlled environment within the sleeve.

In a particularly preferred embodiment of the invention the sleeve is of a flexible material. Most preferably, the sleeve is of a gas-impermeable material to create a controlled pressurised environment within the sleeve.

In a particularly preferred embodiment of the invention the sleeve comprises a generally cylindrical body closed at one end thereof and an exit opening is provided in a side wall of a body adjacent the closed end.

In one arrangement the exit sealing means comprises a flange around the exit for sealing against the body of a patient. Preferably the flange is provided with an adhesive for adhering to the body. Typically the exit and flange are covered by a peel-off cover.

In another arrangement the flange is engaged with a mounting ring surrounding an incision in a patient's body.

The entry sealing means may comprise a valve means through which a surgeon passes an arm. Preferably the valve means is of a material which is sufficiently flexible to allow an arm to be passed therethrough and to seal against the arm when passed therethrough.

Alternatively, the means comprises a first mounting in the sleeve entry, a second mounting and a sealing body of flexible material extending between the mountings, one of the mountings being twisted relative to the other two to twist the sealing body into engagement with an arm passing therethrough.

In one arrangement fixing means are provided for fixing one mounting relative to the other in the sealing position. Typically the fixing means comprises inter-engaging formations provided on the mountings.

In another arrangement the first mounting comprises a ring mounted in the sleeve at: the entry thereof.

In a particularly preferred arrangement the second mounting comprises a ring to which the sealing material is attached.

In one embodiment of the invention the entry sealing means comprises a first sealing element provided in the entry and a second sealing entry provided, on a surgical glove, the sealing elements inter-engaging to seal the sleeve on passing of the glove through the entry.

According to another aspect of the invention there is provided a valve comprising an outer ring and a sealing sleeve of flexible material mounted to the ring and extending into the opening defined by the ring to terminate in a substantially centrally disposed inlet opening through which a member such as a trocar or surgical instrument may be passed, the sealing body remaining in sealing engagement with the member as it is passed therethrough.

In a particularly preferred embodiment of the invention, the sealing body is twisted into a substantially hourglass shape having a central opening through which a member is passed.

Preferably the ring comprises a pair of axially facing ring parts, opposite free ends of the flexible sealing sleeve being attached to the respect ring parts, one of the ring parts being rotated relative to the other to twist the sealing sleeve into a twisted sealing configuration and fixed relative to the other ring part in the sealing configuration.

The invention also provides a trocar tube or cannula incorporating a valve according to the invention. The invention further provides a trocar assembly incorporating a trocar tube or cannula according to the invention and/or a valve according to the invention.

The invention will be more clearly understood from the following description thereof, given by way of example only with reference to the accompanying drawings in which:—

FIG. 1 is a plan view of a sleeve;

FIG. 2 is a cross-sectional view of the sleeve of FIG. 1;

FIG. 3 is a plan view of a sleeve with an entry sealing means in position;

FIG. 5 is a perspective view of the entry sealing means used in the sleeve of FIGS. 3 and 4 in an open configuration;

FIG. 6 is a side elevational view of the sealing means of FIG. 5 in an intermediate position;

FIG. 7 is a perspective view of the sealing means of FIG. 5 in a sealed configuration;

FIG. 8 is a perspective view of another sleeve according to the invention; and

FIG. 9 is a side cross-sectional view of a further sleeve according to the invention.

FIG. 10 is a side cross-sectional view of one further sleeve according to the invention and FIG. 10a is a rear end view of the sleeve shown in FIG. 10;

FIG. 11 is a diagrammatic exploded perspective view of a trocar assembly incorporating a valve according to the invention;

FIG. 12 is a cross sectional view of a valve used in the assembly of FIG. 1;

FIG. 13 is a perspective view of a trocar tube incorporating the valve;

FIG. 14 is a cross sectional view of the trocar and valve in use;

Figure 4:
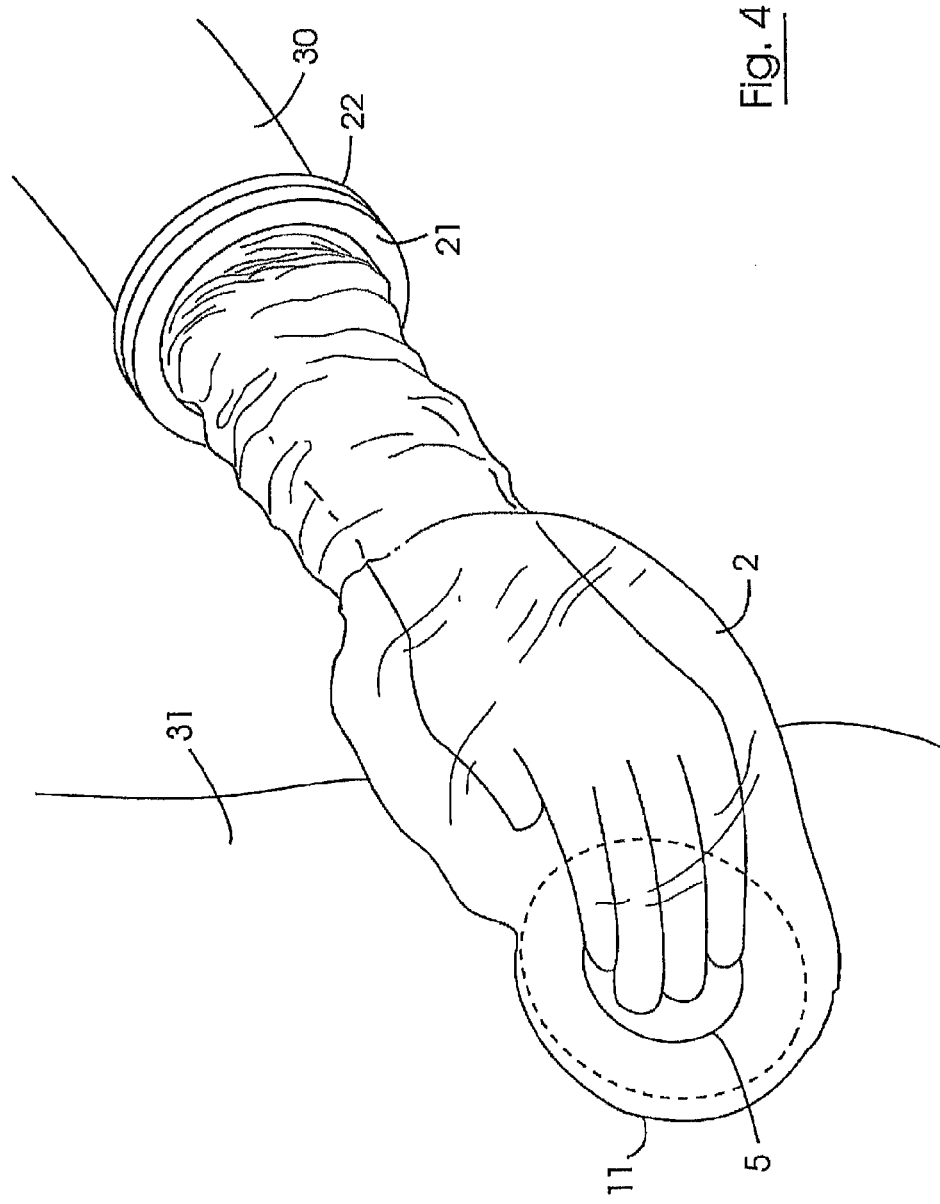
FIG. 4 is a perspective view of the sleeve of FIG. 3 in use.
Figure 15:
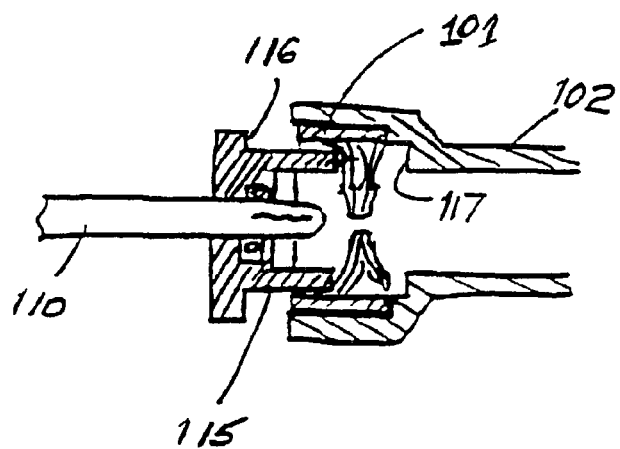
FIG. 15 is a cross sectional view of a modified arrangement according to the invention in one position of use.

Referring to the drawings and initially to FIGS. 1 to 7 thereof, there is illustrated an apparatus for use in surgery according to the invention indicated generally by the reference numeral 1. The apparatus 1 comprises a sleeve 2 of flexible gas-impermeable material. The sleeve 2 in this case comprises a generally cylindrical body closed at one end 3 thereof and open at the other end 4 thereof to define an entry opening at an outer end for passage of an instrument and/or surgeon's arm. An exit opening 5 is provided in a side wall of the sleeve 2 as illustrated particularly in FIG. 2 to provide an access point for entering a patient's body through an incision therein.

Exit sealing means 10 for sealing the exit opening 5 to a patient's body is in this case provided by a flange 11 around the exit opening 5 to the outer face of which is applied a pressure sensitive adhesive for adhering to the body of the patient. The adhesive side of the flange 11 is covered prior to use with a peel-off cover 12.

Entry sealing means which for clarity is not illustrated in FIGS. 1 and 2 is in this case provided by a valve means indicated generally by the reference numeral 20 and illustrated particularly in FIGS. 3 to 7. The valve means 20 comprises a first mounting provided by a ring 21 attached to the body of the sleeve 2 at the entry 4 and a second mounting provided by another ring 22 which is attached to the first ring 21 by a sealing member 23 of flexible material extending between the rings.

The outer ring 22 with the flexible body 23 attached is rotated to twist the sealing body 23 in the direction of the arrow X illustrated in FIG. 6 to engage and seal against a surgeon's arm 30 passing therethrough. When the sealing member 23 is in sealing engagement the outer ring 22 is pushed forwardly in the direction of the arrow Y against the inner ring 21 and the rings are engaged together to maintain the sealing engagement.

Fixing means for preventing rotation of the rings 21, 22 relative to one another when the rings are in the sealing position illustrated in FIG. 7 is in this case provided by a plurality of projections 27 on one of the rings, 22 which are engageable with a plurality of complimentary shaped recesses 28 in the other rings 21 to lock the rings 21,22 against rotation in the sealing position.

In use, an incision is first made in a patient 31. The cover 11 is then removed and the flange 12 is adhesively bonded to the patient around the incision as illustrated particularly in FIG. 4. The sleeve is arranged so that the exit opening 5 is aligned with the incision in the patient 31. With the entry sealing means 20 in the open non-sealing configuration illustrated in FIGS. 3 and 5 a surgeon passes his hand and arm 30 through the entry 4 and the exit opening 5 to enter the patient's body through the incision. When the surgeon's arm 30 has passed through the sealing means 20 a desired distance, the outer ring 22 with the sealing body 23 attached is rotated to twist the sealing body 23 to engage against the surgeon's arm 30 until a relatively tight seal is obtained. The ring 22 is then pushed forwardly against the ring 21 and the projections are engaged in the recesses 28 to lock the rings 21, 22 together against rotation in the sealing configuration. In the case of bowel resection surgery, gas is pumped into the patient's body cavity where the surgery is to be performed, the gas exiting through the incision in the patient and the opening 5 into the sleeve 2 to create a controlled pressurised environment in the sleeve 2 in which the sleeve 2 is inflated. The surgeon carries out the surgery as required and when completed the ring 22 is released from the ring 21 and contra-rotated until the flexible body 23 is in the non sealing position allowing the surgeon to extract his hand through the sleeve 2.

There are many advantages of the invention. Because a surgeon need only make a relatively small incision the trauma to the patient is minimised, there is less risk of damage to the immune system and the healing time is short with a consequent decrease in the length of the hospital stay required. The techniques are considerably simpler than conventional laproscopic surgical techniques and can be readily performed by a surgeon with minimal additional training. A wide range of operations can be performed using the apparatus of the invention.

Referring to FIG. 8 there is illustrated another apparatus for use in surgery according to the invention indicated generally by the reference numeral 50. The apparatus 50 is similar to the apparatus described above with reference to FIGS. 1 to 4 and like parts are assigned the same reference numerals. In this case the entry sealing means comprises a first ring 51 mounted to the sleeve 2 at the entry 4 and a second separate ring 52 at the free end of a surgical glove 53. When a surgeon's arm with the glove 53 passes through the entry 5 the rings 51, 52 are arranged to sealingly engage to create a controlled environment within the sleeve 2 during an operation.

Referring to FIG. 9 there is illustrated, a further apparatus according to the invention for use in surgery and indicated generally by the reference, numeral 60. In this case, the exit sealing means, comprises a sealing diaphragm having a first ring 61 attached to the sleeve 2 and a flexible diaphragm 62 extending from the ring 61 and terminating in an inner or distal ring 63 which is inserted through the incision to engage with the body tissue 30 as illustrated. The sealing diaphragm seals the exit 5 of the sleeve 2 to the incision in the patient's body to create a controlled pressurised environment in the sleeve 2, the controlled pressurised environment being represented by arrows in FIG. 9.

With reference to FIGS. 10 and 10a, the sleeve 70 is an impermeable and flexible sleeve, one end of which is configured to provide a pressure tight seal against a surgeons forearm with the other end configured to provide a pressure tight seal with a patients skin. With the sleeve 70, and integral with it, is a non-return valve 74, in the form of a sealing cuff, permitting the removal of a surgeons hand and forearm from the sleeve whilst maintaining pressure within a patients abdomen.

The sleeve 70, in overall shape and method of construction, is substantially equivalent to known colostomy bags, a differing in that its overall length is greater, there is the integral non-return valve 74 and the open end permits attachment to a surgeons forearm. The sleeve comprises two layers of medical grade polyethylene, one with an orifice 71, edge welded using a radio frequency (RF) welding technique. An annular flange 72 of medical grade polyethelene, one surface of which is coated with medical grade adhesive, is welded to the sleeve as shown. The non-return valve 74 comprises two layers of medical grade polyethelene welded to the sleeve to form the valve indicated. The arm attachment device consists of two rigid medical grade polyethelene circular members 76,77 connected, as indicated, by a thin walled cylindrical tube 78 of elastomer (medical grade latex or similar).

Rotation of member 76 relative to 77 causes the latex tube to form an iris diaphragm effectively reducing the size of the arm access opening. Attachment of member 77 to the sleeve is achieved using medical grade adhesive.

The technique of attachment of this device to a patient is similar to that of a colostomy bag. The annular, adhesive coated flange is applied to a patients skin such that the annulus encircles the access incision. Adhesion may be assisted by the application of an adhesive surgical drape prior to making said incision. Attachment to a surgeons forearm is achieved by inserting a hand and forearm into the sleeve through member 76. Rotation of member 76 relative to member 77 causes an iris diaphragm to form effectively gripping the forearm with the elastomer sleeve. Further movement of the hand towards opening 71 causes the non-return valve 74 to open and access to the abdominal cavity is possible through the access incision. Removal of a surgeons hand is in the reverse order to that above with the result that the non-return valve 74 closes maintaining abdominal pressure.

It is anticipated that in some cases adhesive may be applied to a patient around the area of an incision to which a sealing ring of the sleeve is to be attached during preparations for an operation. Adhesive may alternatively or additionally be applied to the ring to be attached around the area of an incision. Either or both layers of adhesive may be covered by a sterile wrapping material through which the incision may be made. Either or both layers of adhesive may be provided with peel off covers.

It will further be appreciated that the sleeve may incorporate an air lock to facilitate changing of an instrument and/or debris such as cancer cells during an operation without breaking the sterilised environment in the sleeve.

The sleeve may be provided with more than one inlet opening for a surgeon's arms and/or instruments.

The sleeve may also be provided with means to create an intermediate pressurised environment by, for example, providing two inlet sealing cuffs spaced-apart along the sleeve. The inner of the cuffs being sealed before the seal provided by the outer cuff is opened.

Referring to FIGS. 11 to 16, and initially to FIGS. 11 and 12 there is illustrated a valve according to the invention indicated generally by the reference numeral to which in this case is used in association with a trocar assembly comprising a trocar tube or cannula 102 and a trocar 103.

The valve 101 comprises an outer ring which in this case comprises a pair of axially facing ring 105, 106 and a sealing sleeve 107 of a flexible material, the free ends 107a, 107b of which are attached to the respective ring parts 105, 106.

To form the valve 101 according to the invention, typically one of the ring parts 105 is rotated relative to the other to twist the flexible sleeve 106 from a substantially cylindrical non-sealing configuration to an hourglass sealing configuration as illustrated particularly in FIG. 12 having a central opening 108 through which a member such as a trocar 103 may be inserted. The ring parts 104, 106 are retained in the sealing configuration illustrated in FIG. 12 by any suitable means such as by adhesive bonding or the like.

The valve 101 is typically housed in a seat 109 of a trocar tube or cannula 102. To pass a member such as a trocar 103, operating instrument 110 or the like through the valve 101 in a trocar tube or cannula 102, the trocar 103 is first offered up to the opening 108 in the sealing sleeve 107 and is pushed through the sleeve 107 by rotating the trocar 103 to ease the passage of the trocar through the sleeve by contra-rotating the sealing sleeve 107 against the sealing twist to enlarge the opening 108. As the trocar 103 passes through the sleeve 108 the sealing engagement is maintained.

Figure 16:
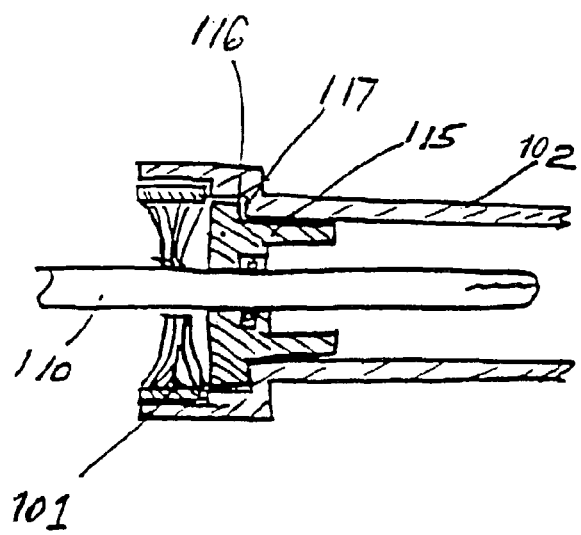
FIG. 16 is a cross sectional view of the arrangement of FIG. 15 in another position of use.

A wide range of different size and types of members such as trocars or operating instruments may be readily passed through a single valve 101. For narrow members such as the instrument 110 illustrated in FIGS. 15 and 16 a collar 115 may be provided around the instrument 110, the collar 115 engaging against the sealing sleeve 107 of the valve 101 to enlarge the opening 108 (see FIG. 5) allowing the collar 115 and instrument 110 to readily pass therethrough (FIG. 16). In the inserted position a shoulder 116 of the collar 115 engages against a stop 117 on the tube 102. When it is desired to withdraw the instrument 10 from the trocar tube 102, the instrument is drawn back to the collar 115 and the collar 115 with the instrument 110 in frictional engagement therewith is drawn back through the flexible sealing sleeve 107.

There are many advantages of the valve according to the invention. For the particular surgical application described, a single trocar tube may now be inserted into a body cavity allowing a wide range of different types and sizes of instruments to be inserted through the tube. Thus, there would be a reduction in the number of trocar assemblies required for a particular operation. In addition, because of the simplicity of construction and operation, the valve and trocar tube or cannula are readily sterilisable and consequently re-usable.

It will be appreciated that while the invention has been specifically described for use with a trocar assembly, it has many different applications and accordingly the invention is not limited to the application of the valve to a trocar tube, cannula or trocar assembly.

It will be appreciated that an additional entry aid may be provided as an alternative to or in addition to the collar just described. The additional sealing may be provided by a plurality of flexible segments extending inwardly on the inlet side of, the valve, the segments being pushed forwardly on insertion of an instrument to engage against and open the valve to facilitate passage through the valve.

The invention is not limited to the embodiments hereinbefore described, which may be varied in construction and detail without departing from the scope of the invention as defined in the appended claims 1 to 24 which are incorporated in this description by reference.

The invention claimed is:

1. A surgical device providing sealed access through an incision in a patient, the device comprising:
   a distal ring insertable through the incision to engage internal body tissue;
   a tubular diaphragm having a distal end, a proximal end, and an incision engaging portion, the distal end of the tubular diaphragm being coupled to the distal ring, the incision engaging portion configured to engage the incision, and the proximal end of the tubular diaphragm located proximal the distal ring and outside the incision; and
   an entry seal assembly located proximal the tubular diaphragm, the entry seal assembly configured to maintain a controlled pressurized environment inside the surgical device such that non-adhesive sealing of the surgical device to the patient is provided by engagement of the incision engaging portion of the diaphragm with the incision and engagement of the distal ring to the internal body tissue, said sealing increasing with an increase in pressure within the controlled pressurized environment.

2. A surgical device as claimed in claim 1, wherein the entry seal assembly includes a first member and a second member connected together by a sleeve member, the first and second members being rotatable relative to one another to seal an object.

3. A surgical device as claimed in claim 2, wherein the first member includes a first ring, and the second member includes a second ring.

4. A surgical device as claimed in claim 3, wherein the first ring includes a circular shape, and the second ring includes a circular shape.

5. A surgical device as claimed in claim 3, wherein the entry seal assembly includes a locking assembly configured to secure the first and second rings together.

6. A surgical device as claimed in claim 1, wherein the entry seal assembly includes a sleeve extending between a seal mechanism and a proximal ring.

7. A surgical device as claimed in claim 6, wherein the proximal ring includes a circular shape, and the distal ring includes a circular shape.

8. A surgical device as claimed in claim 7, wherein the proximal ring, distal ring, and diaphragm have approximately the same inner diameter.

9. A surgical device as claimed in claim 1, wherein the entry seal assembly includes a first component and a second component, the first component being completely detachable from the second component.

10. A surgical device as claimed in claim 9, wherein the first component includes a surgical glove.

11. A surgical device as claimed in claim 1, wherein the entry seal assembly is configured to receive and seal at least part of a human arm.

12. A surgical device as claimed in claim 1, wherein the entry seal assembly is configured to receive and seal at least part of an instrument.

13. A surgical device as claimed in claim 1, wherein the entry seal assembly is movable between an unsealed configuration and a sealed configuration, and the entry seal assembly includes a locking assembly configured to secure the entry seal assembly in the sealed configuration.

14. A surgical device as claimed in claim 1, wherein the entry seal assembly forms a proximal-most portion of the surgical device.

15. A surgical device providing sealed access through an incision in a patient, the device comprising:
    a distal ring insertable through the incision to engage internal body tissue;
    a tubular diaphragm having a distal end, a proximal end, an internal portion, and an incision engaging portion opposite the internal portion, the distal end of the tubular diaphragm being coupled to the distal ring and the proximal end of the tubular diaphragm located proximal the distal ring and outside the incision; and
    an entry seal assembly located proximal the tubular diaphragm and configured to maintain a controlled pressurized environment inside the surgical device such that non-adhesive sealing of the surgical device to the patient is provided, the engagement of the distal ring to the internal body tissue providing a seal such that the incision engaging portion of the tubular diaphragm is not subject to the controlled pressurized environment, while the internal portion of the tubular diaphragm is subject to the controlled pressurized environment.

16. A surgical device as claimed in claim 15, wherein the entry seal assembly includes a first member and a second member connected together by a sleeve member, the first and second members being rotatable relative to one another to seal an object.

17. A surgical device as claimed in claim 16, wherein the first member includes a first ring, and the second member includes a second ring.

18. A surgical device as claimed in claim 17, wherein the first ring includes a circular shape, and the second ring includes a circular shape.

19. A surgical device as claimed in claim 17, wherein the entry seal assembly includes a locking assembly configured to secure the first and second rings together.

20. A surgical device as claimed in claim 15, wherein the entry seal assembly includes a sleeve extending between a seal mechanism and a proximal ring.

21. A surgical device as claimed in claim 20, wherein the proximal ring includes a circular shape, and the distal ring includes a circular shape.

22. A surgical device as claimed in claim 21, wherein the proximal ring, distal ring, and diaphragm have approximately the same inner diameter.

23. A surgical device as claimed in claim 15, wherein the entry seal assembly includes a first component and a second component, the first component being completely detachable from the second component.

24. A surgical device as claimed in claim 23, wherein the first component includes a surgical glove.

25. A surgical device as claimed in claim 15, wherein the entry seal assembly is configured to receive and seal at least part of a human arm.

26. A surgical device as claimed in claim 15, wherein the entry seal assembly is configured to receive and seal at least part of an instrument.

27. A surgical device as claimed in claim 15, wherein the entry seal assembly is movable between an unsealed configuration and a sealed configuration, and the entry seal assembly includes a locking assembly configured to secure the entry seal assembly in the sealed configuration.

28. A surgical device as claimed in claim 15, wherein the entry seal assembly forms a proximal-most portion of the surgical device.

29. A surgical device as claimed in claim 15, wherein the distal ring is larger than the incision.

* * * * *

UNITED STATES PATENT AND TRADEMARK OFFICE
CERTIFICATE OF CORRECTION

PATENT NO. : 8,752,553 B2
APPLICATION NO. : 10/600812
DATED : June 17, 2014
INVENTOR(S) : Bonadio et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1860 days.

Signed and Sealed this
Twenty-sixth Day of May, 2015

Michelle K. Lee
*Director of the United States Patent and Trademark Office*